(12) United States Patent
Nesler et al.

(10) Patent No.: US 10,046,108 B2
(45) Date of Patent: Aug. 14, 2018

(54) COMPACT INTRAVENOUS PUMP AND MEDICATION CONTAINER HOLDER

(71) Applicants: Richard Nesler, Placerville, CA (US); Anita Nesler, Placerville, CA (US)

(72) Inventors: Richard Nesler, Placerville, CA (US); Anita Nesler, Placerville, CA (US)

(*) Notice: Subject to any disclaimer, the term of this patent is extended or adjusted under 35 U.S.C. 154(b) by 0 days.

(21) Appl. No.: 15/089,225

(22) Filed: Apr. 1, 2016

(65) Prior Publication Data

US 2016/0287781 A1 Oct. 6, 2016

Related U.S. Application Data

(60) Provisional application No. 62/141,364, filed on Apr. 1, 2015.

(51) Int. Cl.
*A47G 23/02* (2006.01)
*A61M 5/14* (2006.01)

(52) U.S. Cl.
CPC ........ *A61M 5/1415* (2013.01); *A61M 5/1417* (2013.01)

(58) Field of Classification Search
USPC ........................................................ 248/146
See application file for complete search history.

(56) References Cited

U.S. PATENT DOCUMENTS

| | | | | |
|---|---|---|---|---|
| 3,298,648 A | * | 1/1967 | Sepanski | A61J 9/06 248/103 |
| 3,829,051 A | * | 8/1974 | Emmons | E06C 7/14 108/152 |
| 4,262,872 A | * | 4/1981 | Kodet | A61G 1/04 248/291.1 |
| 4,457,502 A | * | 7/1984 | Beach | A47B 3/087 269/11 |
| 4,557,453 A | * | 12/1985 | McCloskey | A61G 7/05 248/283.1 |
| 4,691,397 A | * | 9/1987 | Netzer | A61G 7/0506 248/214 |
| 5,094,418 A | * | 3/1992 | McBarnes, Jr. | A61G 7/0503 248/125.1 |
| 5,114,023 A | * | 5/1992 | Lavin | A47B 57/54 211/107 |
| 5,222,946 A | | 6/1993 | Kamen | |
| D346,655 S | * | 5/1994 | Harris | D24/128 |
| 5,337,992 A | * | 8/1994 | Pryor | A61M 5/1415 248/125.1 |
| 5,399,166 A | | 3/1995 | Laing | |

(Continued)

*Primary Examiner* — Monica E Millner

(74) *Attorney, Agent, or Firm* — Daniel Boudwin; Global Intellectual Property Agency, LLC.

(57) ABSTRACT

A compact intravenous pump and medication container holder. The present invention has a substantially flat base having a peripheral edge with one or more sidewalls placed along the edge. The sidewalls are positioned substantially perpendicular to the base, forming an interior adapted to removably secure an intravenous pump. An arm is placed substantially perpendicular to the base on one side thereon and extends upward therefrom. The arm has a first end secured to the base, and a second end having a fastener adapted to support a medication container. A strap is affixed to one side of the base and is adapted to secure an intravenous pump to the base.

9 Claims, 5 Drawing Sheets

(56) References Cited

U.S. PATENT DOCUMENTS

| | | | | |
|---|---|---|---|---|
| 5,470,037 A * | 11/1995 | Willis | | A61G 7/0503 248/125.9 |
| 5,845,351 A * | 12/1998 | Berta | | A61G 1/04 5/503.1 |
| 5,857,685 A * | 1/1999 | Phillips | | A61M 5/1415 248/129 |
| 5,876,016 A * | 3/1999 | Urban | | A61M 3/0266 248/159 |
| 6,007,124 A | 12/1999 | Thies, Jr. | | |
| 6,390,311 B1 * | 5/2002 | Belokin | | A61M 5/1415 211/189 |
| 6,431,392 B1 * | 8/2002 | Eisenbeisz | | B44D 3/126 220/737 |
| 6,585,206 B2 * | 7/2003 | Metz | | A61G 7/0503 248/121 |
| 6,619,599 B2 * | 9/2003 | Elliott | | A61M 5/1415 248/125.8 |
| 6,708,991 B1 * | 3/2004 | Ortlieb | | A61M 5/1415 248/122.1 |
| 7,354,023 B1 * | 4/2008 | Wappler | | B25H 3/06 248/206.5 |
| 7,527,600 B2 * | 5/2009 | Farmer | | A47B 57/565 362/257 |
| 7,575,261 B2 * | 8/2009 | Gagne | | B44D 3/126 16/422 |
| 8,104,729 B2 * | 1/2012 | Walke | | A61G 12/002 248/125.1 |
| 8,235,402 B2 * | 8/2012 | Knappe | | A61G 12/001 280/47.26 |
| D692,132 S * | 10/2013 | Damron | | D24/128 |
| 8,671,847 B2 * | 3/2014 | Lymberis | | A47B 96/025 108/42 |
| 8,915,478 B2 * | 12/2014 | Perez | | A61G 1/04 248/178.1 |
| 9,033,162 B2 * | 5/2015 | Brotzman | | A61B 19/0256 211/126.14 |
| 9,051,959 B2 * | 6/2015 | Davis | | F16B 45/00 |
| 9,291,305 B2 * | 3/2016 | Brehm | | F16M 13/022 |
| 2002/0101046 A1 * | 8/2002 | Potter | | A61G 1/04 280/47.34 |
| 2003/0046764 A1 * | 3/2003 | Smeed | | A61G 1/04 5/503.1 |
| 2005/0040126 A1 * | 2/2005 | Gaster | | A61M 5/1415 211/207 |
| 2009/0301927 A1 * | 12/2009 | Fvlbrook | | A61B 90/57 206/564 |
| 2012/0118650 A1 | 5/2012 | Gill | | |
| 2012/0289927 A1 | 11/2012 | Siew Kuang Choong | | |

* cited by examiner

COMPACT INTRAVENOUS PUMP AND MEDICATION CONTAINER HOLDER

CROSS REFERENCE TO RELATED APPLICATIONS

This application claims the benefit of U.S. Provisional Application No. 61/141,364 filed on Apr. 1, 2015. The above identified patent application is herein incorporated by reference in its entirety to provide continuity of disclosure.

BACKGROUND OF THE INVENTION

The present invention relates to intravenous delivery devices. More specifically, the present invention relates to an intravenous pump and medication container holder that is compact and can be easily transported by a user.

A common method of delivering medication to a patient involves directly administering a liquid form of a drug intravenously into the bloodstream. The advantages offered by this delivery method involve expedited distribution of the medication to the bloodstream in comparison to other methods as well as the ability to slowly administer specific amounts of medication over an elongated period of time. Often a bag or bottle of medication is suspended from a mobile rack and a tube is connected to the medication bag or bottle at one end and to a patient via an intravenous catheter at another end. The medication is then slowly released to the patient.

Because this method relies on gravity to deliver the medication to the patient, the source of medication must be constantly placed above the insertion point of the catheter. This is often accomplished by suspending the medication on a tall mobile rack. However, this presents a number of difficulties. While many mobile racks have wheels installed thereon to allow the rack to be easily transported, the wheels are often only designed to be used on a smooth hard floor with minimal transitions. Obstacles such as carpeting or dividers placed between rooms can make maneuvering the mobile rack difficult, especially for weaker patients. Additionally, because the rack must be a certain height to ensure the raised level of the medication, it is difficult to use the rack in confined spaces such as the interior of a vehicle.

In order to overcome these issues, intravenous pumps have been used to administer medication without the need for the medication source to be placed above the insertion point. However, these pumps can be cumbersome and are not easily carried on their own. Furthermore, these intravenous pumps do not provide a place for a medication bag or bottle to be attached thereto. Thus, a device for supporting both an intravenous pump and a medication container is desired in order to improve portability and allows the patient to move more freely.

SUMMARY OF THE INVENTION

In view of the foregoing disadvantages inherent in the known types of intravenous delivery devices now present in the prior art, the present invention provides an intravenous delivery device wherein the same can be utilized for providing convenience for the user when delivering medication to a patient through an intravenous pump. The present invention comprises a substantially flat base having a peripheral edge with one or more sidewalls disposed along the edge. The sidewalls are positioned substantially perpendicular to the base, forming an interior adapted to accept an intravenous pump. An arm is positioned substantially perpendicular to the base on one side thereon and extends upward. The arm has a first end secured to the base, and a second end further comprising a fastener adapted to support a medication container. A strap is affixed to one side of the base, and is adapted to secure an intravenous pump to the compact intravenous pump and medication container holder.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
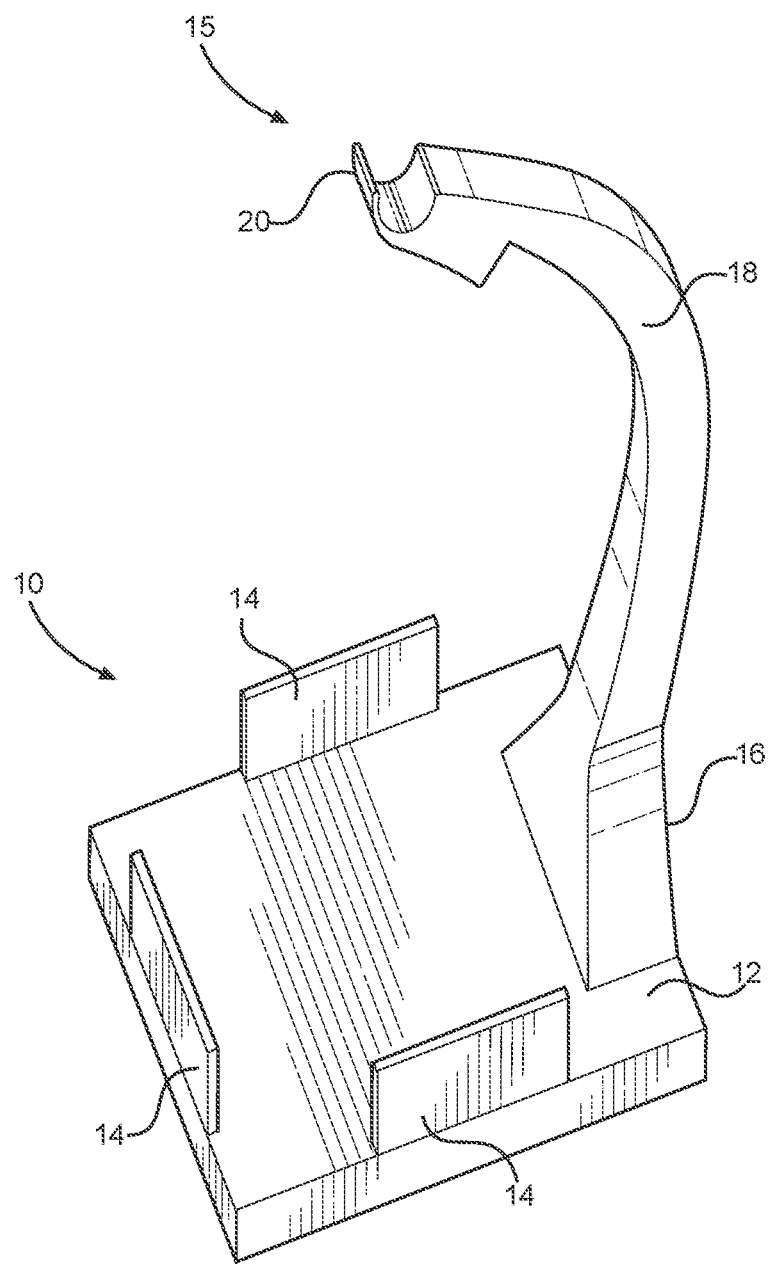
FIG. 1 shows a perspective view of an embodiment of the compact intravenous pump and medication container holder.

Reference is made herein to the attached drawings. Like reference numerals are used throughout the drawings to depict like or similar elements of the compact intravenous pump and medication container holder. The figures are intended for representative purposes only and should not be considered to be limiting in any respect.

Figure 2:
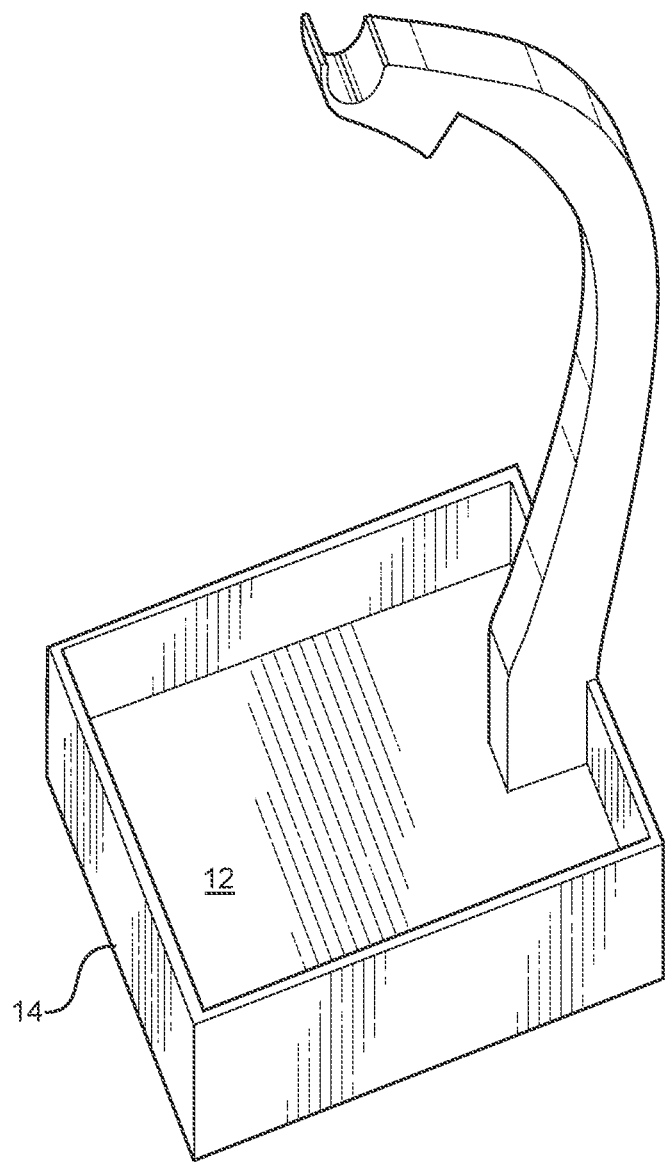
FIG. 2 shows a perspective view of an alternative embodiment of the compact intravenous pump and medication container holder with a continuous side wall.

Referring now to FIGS. 1-2 there are shown perspective views of embodiments of the compact intravenous pump and medication container holder. The compact intravenous pump and medication container holder 10 comprises a base 12 that is substantially flat and has a peripheral edge. One or more sidewalls 14 are disposed along the peripheral edge. In one embodiment of the compact intravenous pump and medication container holder 10, the sidewalls comprise multiple segments disposed along the peripheral edge of the base. In an alternative embodiment of the compact intravenous pump and medication container holder 10, the sidewalls 14 form one continuous wall along the perimeter of the peripheral edge of the base 12. A rigid arm 18 having a first end 16 secured to the peripheral edge of the base 12 and a second end 15 that extends vertically above the base 12. The second end 15 of the arm 18 comprises a fastener 20 that is adapted to secure a medication container thereto.

The base 12 is adapted to store or hold an intravenous pump therein. A medication container such as a bag or a bottle of intravenous fluid is secured to the fastener 20 at the second end 15 of the arm 18. Medication is drawing into the pump, and then administered to a patient at a rate controlled by the pump settings. The arm 18 of the compact intravenous pump and medication container holder 10 allows the medication source to remain located above the pump input at all times, ensuring a continuous flow of medication to the pump without introducing air bubbles to the flow of medication, which could cause a pump to malfunction.

Figure 3:
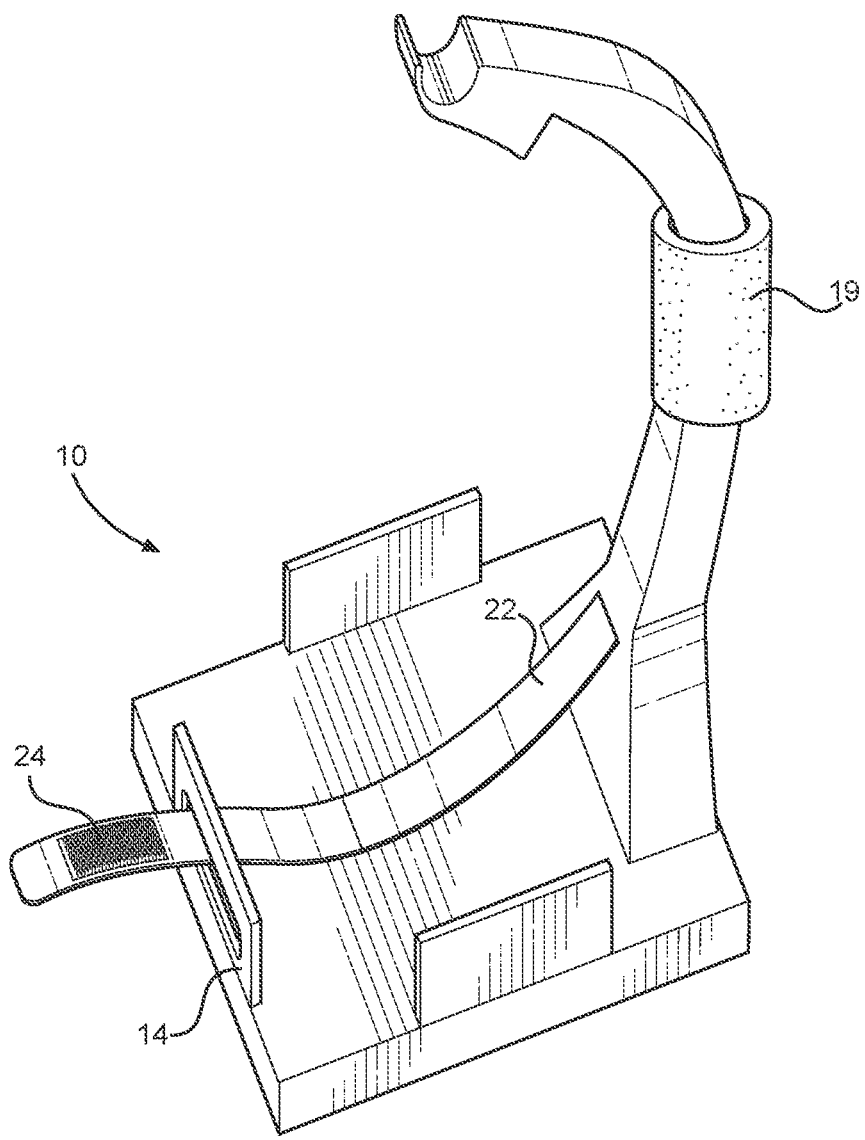
FIG. 3 shows a perspective view of an alternative embodiment of the compact intravenous pump and medication container holder with a securing strap.

Referring now to FIG. 3 there is shown a perspective view of an alternative embodiment of the compact intravenous pump and medication container holder. Some embodiments of the compact intravenous pump and medication container holder 10 further comprise a strap 22 configured to provide additional support to secure a pump to the base 12. In one embodiment, a first end of the strap 22 is permanently affixed to the first end of the arm 16. In another embodiment, the first end of the strap 22 is secured directly to the base 12. A fastener 24, such as a hook and loop fastener, is disposed on the second end of the strap 22. The second end of the strap 22 can be secured to the base 12 of the compact intravenous pump and medication container holder 10. In this embodiment, there is a matching fastener disposed on the base 12 adapted to attach to the second end of the strap 22. In some embodiments of the compact intravenous pump and medication container holder 10, the sidewall 14 substantially opposite the first end of the strap 22 further comprises a slot 24 adapted to have the strap 22 inserted therein. In this configuration, the strap 22 can secure a pump by extending over the pump, through the slot 24, and folded and secured back onto itself. Additionally, the arm can have a soft grip padding 19 or similar material disposed thereon to provide a comfortable handle.

Figure 4A:
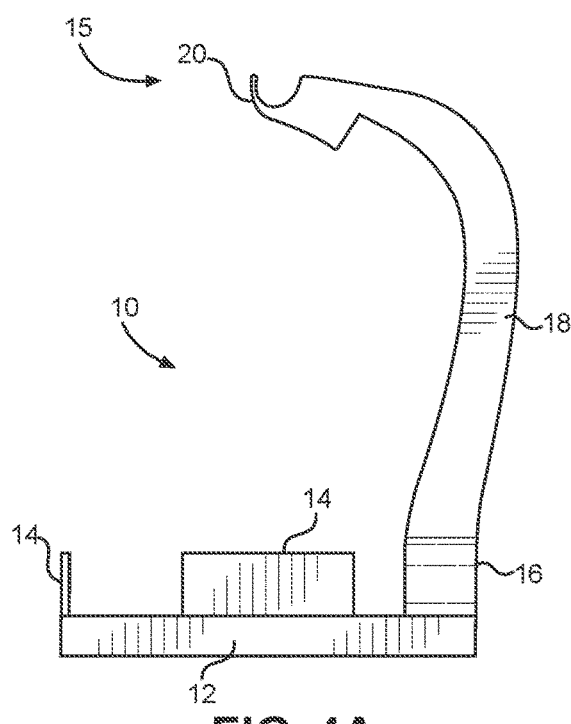
FIGS. 4A and 4B show side views of two embodiments of the compact intravenous pump and medication container holder with alternate fasteners disposed on the arm.
Figure 4B:
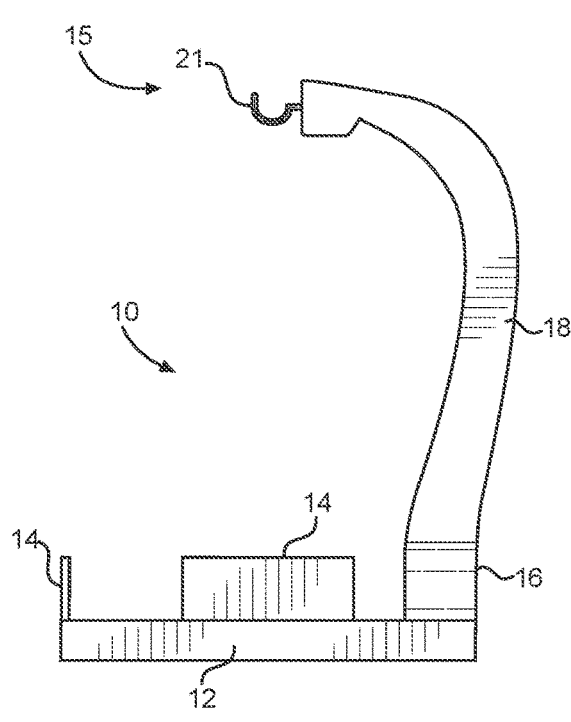

Referring now to FIGS. 4A and 4B there are shown side views of the compact intravenous pump and medication container holder. The arm 18 height is dimensioned such that when a medication bag is suspended from the fastener 20 and 21, the bag does not contact the base and hangs freely from the fastener 20 and 21. In this way, the bag does not interfere with or come into contact with a pump disposed on the base. In some embodiments of the compact intravenous pump and medication container holder 10, the fastener 20 on the second end of the arm 15 is a notch integral to the arm 18 and configured to secure a medication container thereto. In other embodiments of the compact intravenous pump and medication container holder 10, the fastener is a hook 21 that is attached to the second end of the arm 18 and configured to secure a medication container thereto.

Figure 5:
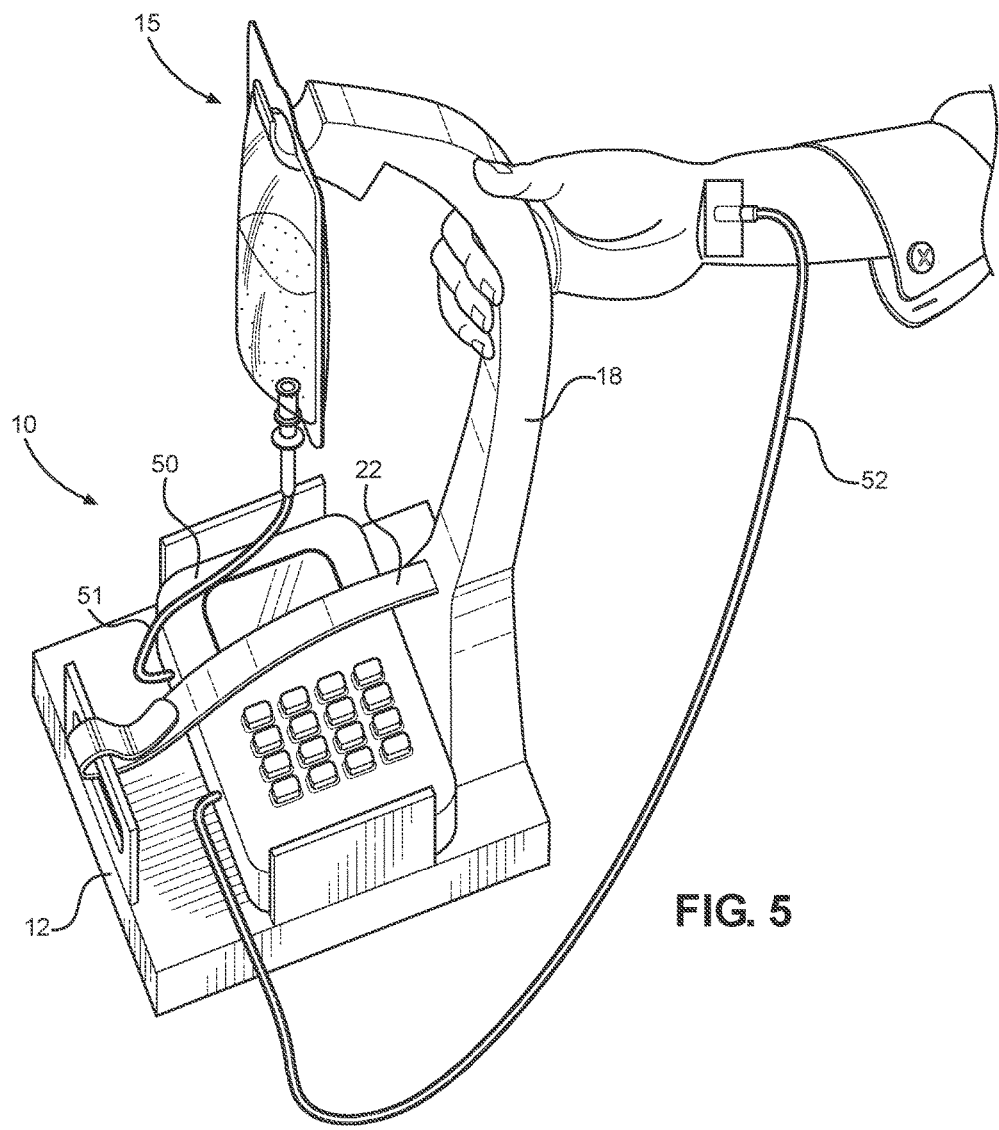
FIG. 5 shows a perspective view of the compact intravenous pump and medication container holder in use.

Referring now to FIG. 5 there is shown a perspective view of the compact intravenous pump and medication container holder in use. In operation, a pump 50 is positioned on the upper surface of the base and secured in position thereon via the strap 22. A bag of intravenous medication is secured to the second end 15 of the arm 18 and hangs above the pump 50. A first length of tube 51 runs from the medication bag to the pump 50 input, and a second length of tube 52 runs from the pump output to a catheter disposed on a limb of a patient. The patient can carry the compact intravenous pump and medication container holder 10 via the arm 18. This allows the patient to easily transport their intravenous medication while it is being administered.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A compact intravenous pump and medication container holder, comprising:
   a base having a peripheral edge, wherein the base is configured to receive the compact intravenous pump thereon;
   a sidewall disposed along the peripheral edge of the base, the sidewall extending perpendicularly upwards from the base;
   an arcuate arm extending vertically from a rear portion of the base in a same direction as the sidewall, the arm including a first end affixed to the base and a second end including a fastener fixedly attached to the second end, the fastener extending outwardly from the second end;
   wherein the fastener is configured to secure the compact intravenous pump to the base;
   the arcuate arm positioned centrally between a pair of opposing sides of the base;
   wherein the arcuate arm defines a curve extending between the first end and the second end, wherein the curve is configured to be grasped by a user such that the compact intravenous pump and medication container holder can be supported by a single hand of the user.

2. The compact intravenous pump and medication container holder of claim 1, wherein the sidewall& comprises a single continuous wall extending along the peripheral edge of the base.

3. The compact intravenous pump and medication container holder of claim 1, wherein the sidewall comprises multiple segments disposed at fixed intervals from each other along the peripheral edge of the base.

4. The compact intravenous pump and medication container holder of claim 1, further comprising a strap including a first end affixed to the first end of the arcuate arm and a second end including a fastener removably securable to the base, the strap extending perpendicularly relative to the arcuate arm and parallel relative to the base.

5. The compact intravenous pump and medication container holder of claim 4, wherein the sidewall comprises a slot configured to accept the second end of the strap therethrough.

6. The compact intravenous pump and medication container holder of claim 1, wherein the arcuate arm further comprises a grip disposed along the curve.

7. The compact intravenous pump and medication container holder of claim 4, wherein the fastener comprises a notch including an arcuate groove configured to receive and suspend a portion of a medication container thereon.

8. The compact intravenous pump and medication container holder of claim 4, wherein the fastener comprises a hook configured to receive and suspend a portion of a medication container thereon.

9. A compact intravenous pump and medication container holder, consisting of:
   a base having a peripheral edge;
   a sidewall disposed along the peripheral edge of the base, the sidewall extending perpendicularly upwards from the base;
   an arcuate arm extending vertically from a rear portion of the base, the arm including a first end affixed to the base and a second end including a fastener fixedly attached to the second end, the fastener extending outwardly from the second end;

wherein the arcuate arm defines a curve extending between the first end and the second end.

\* \* \* \* \*